United States Patent [19]

Ardaillon et al.

[11] Patent Number: 5,296,219
[45] Date of Patent: Mar. 22, 1994

[54] PROCESS FOR COATING ACTIVE PRINCIPLES USING A PH-SENSITIVE POLYMER

[75] Inventors: Pierre Ardaillon, Saint-Priest; Christian Prud'Homme, Lyons, both of France

[73] Assignee: Rhone-Poulenc Nutrition Animale, Commentry, France

[21] Appl. No.: 17,445

[22] Filed: Feb. 12, 1993

Related U.S. Application Data

[63] Continuation of Ser. No. 707,491, May 30, 1991, abandoned.

[30] Foreign Application Priority Data

Jun. 15, 1990 [FR] France .................. 90 07584

[51] Int. Cl.$^5$ .................................................. A61K 9/24
[52] U.S. Cl. .............................. 424/78.01; 424/468; 424/482; 514/964; 523/105
[58] Field of Search ............ 424/438, 482, 474, 78.01, 424/468; 514/964; 523/105

[56] References Cited

U.S. PATENT DOCUMENTS

| | | | |
|---|---|---|---|
| 2,799,241 | 7/1957 | Wurster | 118/324 |
| 4,181,708 | 1/1980 | Dannelly | 424/438 |
| 4,181,709 | 1/1980 | Dannelly | 424/438 |
| 4,764,364 | 8/1988 | Heller | 523/105 |
| 4,780,315 | 10/1988 | Wu et al. | 424/438 |
| 4,800,087 | 1/1989 | Mehta | 424/497 |
| 4,832,967 | 5/1989 | Autant | 426/310 |
| 4,855,132 | 8/1989 | Heller | 523/105 |
| 4,876,097 | 10/1989 | Autant | 424/438 |
| 4,877,621 | 10/1989 | Ardaillon | 424/438 |

FOREIGN PATENT DOCUMENTS 0231817 1/1987 European Pat. Off. .

*Primary Examiner*—Thurman K. Page
*Assistant Examiner*—Raj Bawa
*Attorney, Agent, or Firm*—Finnegan, Henderson, Farabow, Garrett & Dunner

[57] ABSTRACT

A process for coating at least one medicinal and/or foodstuff active principle useful for ruminants. At least one monomer is polymerized in an oil-in-water emulsion in the presence of a surfactant to synthesize a pH-sensitive-polymer composition, the composition being obtained in an oil-in-water emulsion. Without isolation of the pH-sensitive polymer, the oil-in-water emulsion is used to coat the active principle, preferably methionine or lysine or a derivative thereof. The pH-sensitive polymer is not dissolved in an organic solvent(s) in either the polymerization or coating steps. The pH-sensitive polymer is stable at pH 6 but at pH 2, the coated active principle is released.

17 Claims, No Drawings

PROCESS FOR COATING ACTIVE PRINCIPLES USING A PH-SENSITIVE POLYMER

This application is a continuation of application Ser. No. 07/707,491, filed May 30, 1991, now abandoned.

The present invention relates to a process for the preparation of a pH-sensitive polymer as well as to a process for coating active principles using this polymer. It relates more particularly to a process for the preparation of the pH-sensitive polymer in emulsion and its use for the coating of medicinal and/or food active principles.

The preparation of a vinylpyridine and styrene-based copolymer by the polymerisation of monomers in emulsion in the presence of a surfactant agent, chosen from among the alkaline salts of fatty acids, and an initiator at a fixed pH between 10 and 14, is known for example according to the U.S. Pat. No. 4,593,082. In all cases, the polymer is recovered by filtration, washed and then dried.

The coating of active principles with pH-sensitive polymers, optionally mixed with a hydrophobic substance such as stearic acid and/or a water-insoluble polymer such as ethyl cellulose has also been known for a long time. These coatings are described in particular in the case of animal nutrition in the patent applications published under the numbers U.S. Pat. No. 4,832,967, EP 260,186 or EP 188,953.

According to these applications, the spherical particles of methionine and/or of lysine are coated by the fluidised bed technique using a solution of pH-sensitive polymer previously synthesised and isolated, for example according to the patent already described, which is then dissolved, for the coating stage, in one or more organic solvents such as halogenated solvents, alcohols or ethers. This technique allows an easy and homogeneous spraying of the pH-sensitive polymer or polymers and additives but presents the disadvantage, from the economic point of view, of having to isolate the polymer and, from the ecotoxicity point of view, of having to use a large quantity of solvents, about 20 to 100 g of solvents for dissolving 1 g of pH-sensitive polymer. It is regrettable to have to use in products intended for animal nutrition solvents whose non-toxicity is not established.

The present invention made it possible to proceed directly to the synthesis of the polymer and to its use for coating without an intermediate isolating stage. This process thus makes it possible to coat active principles such as amino acids or vitamins whilst avoiding isolating the polymer and all usage, during the coating stage, of organic solvents which are incompatible with biological media.

In fact, the present invention relates to a process for coating, using a pH-sensitive-polymer-based composition, medicinal and/or food active principles, characterised in that, in a first stage, a monomer or a mixture of monomers, whose polymerisation allows the synthesis of the pH-sensitive polymer, is polymerised in aqueous emulsion in the presence of a surfactant agent and then, in a second stage, the aqueous emulsion of the pH-sensitive polymer, after the optional addition of supplementary coating agents, is deposited on the said active principles without intermediate isolation. It is altogether surprising that the process can be implemented despite the high water-solubility of some active principle, for example, lysine and its derivatives in particular. The medicinal and/or food active principles to be coated exist preferably in the form of spherical or ovoid granules in particular, with a diameter of between 0.3 and 3 mm.

The coating, using the aqueous polymerisation emulsion, allows a substantial economy in the implementation of the process since it avoids the polymer-isolating operation, the use of polymer-redissolving solvent and the consequent use of solvent-recovery installations which are expensive from the point of view of security and investment. It also allows productivities to be increased relative to prior art processes.

The pH-sensitive polymers used in the process according to the invention and whose preparation is carried out by polymerisation in emulsion are chosen in particular from among:

- acetylacetic ester polyvinyl acetals substituted by dialkylated nitrogenised groups such as the diethylamino group,
- copolymers of dialkylaminoalkyl acrylates and methacrylates and of an acrylic or methacrylic ester or acid,
- copolymers of styrene or acrylonitrile with the isomers or the derivatives of vinylpyridine.

Among all the polymers mentioned, the use of copolymers of styrene and vinylpyridine is preferred, and more particularly the styrene and 2-vinyl-pyridine-based copolymer.

The preparation of the polymer is carried out in a conventional manner by bringing into contact the monomer or monomers in the presence of a surfactant agent and a polymerisation initiator. The surfactant agents are preferably chosen from among the alkaline salts of fatty acids, the use of the sodium salt of oleic acid is more particularly preferred. The polymerisation initiator is chosen from among the soluble initiators conventionally used in emulsion processes, the use of sodium persulphate is more particularly preferred. The pH during the course of the polymerisation is preferably maintained between 10 and 14 and more particularly between 11 and 13.

The medicinal active principles which may be coated by the process of the invention are chosen in particular from among vitamins, antibiotics antiparasitic compounds and hormones. The foodstuff active principles are chosen in particular from among essential amino acids which are presumed to be limiting, such as methionine and/or lysine and/or tryptophan.

To these active principles may be added optionally lamellar loadings which facilitate disintegration in the digestive tract. These loadings are chosen in particular from among pH-sensitive or non-pH-sensitive loadings such as for example: talc and/or silica and/or carbonates and/or complex polyphosphates such as those based on $Na_2O$, $CaO$, $P_2O_5$ and $A_2O_3$. To these active principles may also be added binding agents chosen from among fatty acids or esters, cellulose (such as that marketed for example under the name Avicel) or its derivatives, particularly ethylcellulose, carboxymethylcellulose, as well as basic copolymers. The whole of the active principle or principles and additives form the core of the granulate which is then coated with previously prepared pH-sensitive-polymer emulsion.

These medicinal or foodstuff active principles, optionally containing an additive and coated with a pH-sensitive polymer, are particularly useful for ruminant nutrition since little or no degradation occurs during the passage through the rumen. They are released inside the rennet-stomach and/or the intestine of ruminants.

The coating process is carried out by deposition of the aqueous polymerisation emulsion containing the pH-sensitive polymer onto the active principle. The coating emulsion may also contain additives such as those previously mentioned, as well as antistatic agents, plasticising agents, colorants or appetising agents and complementary emulsifying agents. By way of coating mixture, the use of an aqueous dispersion containing the pH-sensitive polymer, a hydrophobic substance, optionally containing a water-insoluble polymer, and an emulsifying agent is preferred.

The hydrophobic substance is preferably selected from fatty acids containing 12 to 22 carbon atoms such as, for example, stearic acid or behenic acid.

The emulsifier may be chosen from among fatty acid esters or fatty acid salts, it may be the same or different from the surfactant agent used during the polymerisation. In the event that it is a fatty acid salt, the emulsifier may be formed "in situ" by salification of the fatty acid by means of a base chosen from among alkaline and ammonium hydroxides.

The water-insoluble polymer is advantageously chosen from among the ethers and the esters of water-insoluble cellulose such as ethyl cellulose, cellulose acetate, cellulose propionate and cellulose acetobutyrate.

According to a preferred embodiment, the coating mixture is prepared by mixing the aqueous polymerisation emulsion and an aqueous solution containing a base so as to trigger the "in situ" formation of the emulsifier, the melted fatty acid and the optional complementary coating agents being introduced into the resulting mixture. According to a variant embodiment, it is obvious that a complement of the emulsifying agent followed by the fatty acid and the complementary coating agents may be introduced into the polymerisation emulsion.

Thus, the coating emulsion contains in particular 1 to 10% by weight, relative to the dry coating composition, of an emulsifier chosen, as previously indicated, from among fatty acid esters or salts.

From a quantitative point of view, the coating emulsion preferably contains:

10 to 70 g of pH-sensitive polymer, 30 to 90 g of one or more hydrophobic substances, 0 to 20 g of one or more water-insoluble polymers per 150 milliliters to one liter of water.

It is obvious that these quantities are preferential indications which will be adjusted by the specialist in relation to the viscosity and the stability of the emulsion.

The emulsion is then deposited on the granules to be coated, for example, according to the fluidised bed technique of the WORSTER type such as described in the U.S. Pat. No. 2,799,241 and EP 188,953. Preferably, a coating layer with a thickness of 5 to 100 microns and more preferably of 40 to 60 microns is deposited.

The granules obtained after coating are used as food supplements or for the medicinal treatment of ruminants.

Their preparation will be more completely described by means of the following examples which should not be considered as implying a limitation to the invention.

EXAMPLE 1

Preparation of an Emulsion of Colpolymer of 2-vinyloyridine and Styrene 150 g of styrene and 350 g of freshly distilled 2-vinylpyridine are mixed. This mixture is washed twice with 160 ml of a 5% aqueous solution of sodium hydroxide and then twice with 320 ml of demineralised water. The monomers thus treated are loaded into a polymerisation reactor purged with nitrogen.

In another vessel, a basic solution of sodium oleate is prepared by pouring 15.25 g of oleic acid into 736 g of demineralised water in which have been previously dissolved 7.7 g of sodium hydroxide pellets. The pouring of oleic acid is performed in ten minutes, at room temperature and under moderate stirring.

The oleate solution thus obtained is then introduced into the polymerisation reactor and mixed with the monomers. The mixture is diluted by adding to it 641 g of demineralised water, and then stirring is introduced at 200 revolutions per minute in order to form an emulsion.

The system is carefully purged by bubbling nitrogen through it, and heating is introduced. When the temperature of the emulsion is stabilised at 50° C., 100 g of an aqueous solution containing 5% of sodium persulphate are poured in in two minutes. The heating at 50° C. and the stirring are maintained for five hours.

After polymerisation, the emulsion is "stripped" using water vapour in order to eliminate traces of residual monomers. An aqueous emulsion of copolymer is thus obtained. Its dry extract concentration is 20.75% by weight and its pH is 13.

A sample of the emulsion is removed in order to characterise the polymer formed. By acidification of this sample, the coagulated polymer is obtained which is separated by filtration on sintered glass, and dried in an oven after several washes with demineralised water.

The dried copolymer, in powdered form, has the following characteristics:

inherent viscosity, measured at 25° C., on a solution of 0.5 g of copolymer in 100 ml of dimethylformamide=1.33 dl/g, molecular mass determined by GPC (Gel Permeation Chromatography) in N-methylpyrrolidone, relative to polystyrene standards:

$Mn = 109000$ g/mole $Mw = 610000$ g/mole

Preparation of the Coating Emulsion 420 g of demineralised water and 1.8 ml of a 10% (p/v) aqueous solution of sodium hydroxide are loaded into a 2-liter glass vessel. 106 g of previously prepared copolymer emulsion are poured, in 1 minute, under moderate stirring, into this mixture heated at 84° C. 88 g of stearic acid marketed by UNICHEMA under the name PRIFAC 2981, previously loaded into a pouring funnel heated to 90° C. by a heating electric cord, is added to this mixture maintained at 80° C.

The pouring is carried out in about minutes, while the mixture is vigorously mixed with a POLYTRON apparatus revolving at 11,000 revolutions/minute. The stirring is maintained for another 2 minutes after the end of the pouring.

An emulsion is thus obtained which is maintained at a temperature greater than 70° C. under moderate stirring (magnetic stirring). The amount of extract in this emulsion is 20.4% (p/p).

Coating of Amino Acid Granules

In this example, the coating emulsion was used within the half hour following the end of its preparation.

500 g of spherical granules with an average diameter of 2 mm and containing 57% of lysine hydrochloride and 16% of methionine are loaded into a UNIGLATT spray-coating apparatus equipped with a WORSTER system.

The emulsion, maintained at 90° C. and gently stirred, is sprayed into the fluidised bed formed by the granules, the spraying conditions being as follows:
quantity of emulsion sprayed: about 320 g
flow rate of the fluidising air: 130 m$^3$/h
temperature of the fluidising air (outlet): 37° C.
pressure of the spraying air: 1.5 bars
temperature of the spraying air: 85° C.
flow rate of the emulsion: 9 ml/min
duration of spraying: 41 min.

The degree of protection offered by the coating film thus deposited is evaluated using an in vitro test consisting of stirring a known quantity of coated granules in an aqueous solution buffered at pH 6 and maintained at 40° C. The quantity of lysine hydrochloride released into the medium is determined after 6 hours and 24 hours. Similarly, the pH-sensitivity of the coating is evaluated using an in vitro test consisting of stirring a known quantity of coated granules in an aqueous solution buffered at pH 2 and maintained at 40° C. The quantity of lysine hydrochloride released into the water is determined after 15 min and 30 min respectively. The results are shown in Table I.

These results reveal a high degree of protection at pH 6, and a high rate of amino-acid release at pH 2.

EXAMPLE 2

Starting with the previously prepared basic copolymer emulsion, Example 1 is repeated, modifying only the duration of storage of the coating emulsion. The latter, instead of being used almost immediately, is first preserved for 48 hours at 72° C. before being sprayed into the fluidised bed of granules.

The coated amino acids are evaluated using the tests described in Example 1. The results shown in Table I reveal patterns of protection at pH 6 and of release at pH 2 which are completely satisfactory for the application.

EXAMPLE 3

The starting point is again the basic copolymer emulsion prepared in Example 1.

Example 1 is repeated, modifying only the dry extract content of the coating emulsion.

The content is varied from 20.4% to 30.2% by using 236 g of demineralised water instead of 420 g for diluting the basic copolymer.

The results of this trial are also presented in Table I.

EXAMPLE 4

The procedures of Examples 1 and 3 are followed.

Only the quantity of demineralised water used for diluting the basic copolymer emulsion in the first phase of the preparation of the coating emulsion is modified.

In this example, 130 g of water were thus used, which led to a final emulsion containing 38.3% of dry extract.

TABLE I

| Sample | Emulsion Dry extract content (% p/p) | Duration of storage (h) before use | Duration of spraying (min) | Amount of coating on the granules (%, weight) | In vitro test: pH 6/40° C. % lysine released after 6 h | 24 h | In vitro test: pH 2/40° C. % lysine released after 15 min | 30 min |
|---|---|---|---|---|---|---|---|---|
| Example 1 | 20.4 | <0.5 | 41 | 11.6 | 2.4 | 5.0 | 92 | 100 |
| Example 2 | 20.7 | 48 | 41 | 10.2 | 0 | 4.5 | 90 | 100 |
| Example 3 | 30.2 | <0.5 | 27 | 10.2 | 1.7 | 3.5 | 90 | 100 |
| Example 4 | 38.3 | <0.5 | 21 | 9.0 | 2.8 | 7.7 | 93 | 100 |

We claim:

1. A process for coating at least one medicinal and/or foodstuff active principle useful for ruminants consisting essentially of the steps of:
   (a) polymerizing at least one monomer in an oil-in-water emulsion in the presence of a surfactant, to synthesize a pH-sensitive-polymer, said synthesized polymer being contained in said oil-in-water emulsion, and
   (b) without isolation of the pH-sensitive polymer, coating said active principle with said oil-in-water emulsion containing said pH-sensitive polymer, wherein said pH-sensitive polymer is not dissolved in an organic solvent or mixture of organic solvents in either step (a) or in step (b), and further wherein said pH-sensitive polymer is stable at pH 6 but wherein at pH 2 said coated active principle is released.

2. A process for coating a methionine or lysine active principle consisting essentially of the steps of:
   (a) polymerizing a mixture of vinylpyridine and styrene in an oil-in-water emulsion in the presence of sodium oleate, to synthesize a vinylpyridine-styrene polymer said synthesized vinylpyridine-styrene polymer being contained in an oil-in-water emulsion,
   (b) adding stearic acid and an aqueous sodium hydroxide solution to said oil-in-water emulsion resulting from step (a) to form an oil-in-water coating emulsion, and
   (c) without isolation of the vinylpyridine-styrene polymer, coating said active principle with said oil-in-water coating emulsion resulting from step (b), wherein said vinylpyridine-styrene polymer is not dissolved in an organic solvent or mixture of organic solvents in any of steps (a)-(c).

3. The process according to claim 2, wherein the active principle coated in step (c) is in the form of granules.

4. The process according to claim 3, wherein said active principle is methionine.

5. The process according to claim 1, further consisting essentially of the step (c) of adding at least one optional coating agent to the emulsion containing said pH-sensitive polymer to form a coating emulsion prior to said coating step.

6. The process according to claim 1, wherein the surfactant utilized in step (a) is sodium oleate.

7. The process according to claim 5, wherein said at least one optional coating agent added in step (c) is selected from a fatty acid containing 12 to 22 carbon atoms and an ether or ester of water-insoluble cellulose polymer.

8. The process according to claim 1, wherein the active principle coated in step (b) is at least one amino acid selected from methionine and lysine.

9. The process according to claim 8, wherein said amino acid is lysine hydrochloride.

10. The process according to claim 7, wherein the fatty acid optional coating agent added in step (c) is stearic acid.

11. The process according to claim 5, further consisting essentially of the step (d) of adding after polymerization step (a) but before coating step (b), an emulsifying agent selected from fatty acid salts or esters, wherein said emulsifying agent is the same as or different from the surfactant used during polymerization step (a).

12. The process according to claim 1, wherein both a loading selected from talc, silica, carbonates or complex polyphosphates and the active principle are coated during said step (b).

13. The process according to claim 12, wherein the loading is a complex polyphosphate based on $Na_2O$, $CaO$, $P_2O_5$ and $Al_2O_3$.

14. The process according to claim 2, wherein said coating step (c) is accomplished by spraying said active principle with said coating emulsion resulting from step (b).

15. The process according to claim 1, wherein the active principle coated in step (b) is in the form of granules.

16. The process according to claim 1, further consisting essentially of the step (c) of adding to the oil-in water emulsion containing said synthesized polymer resulting from step (a) at least one antistatic agent, plasticizing agent, colorant or appetizing agent prior to said coating step (b).

17. The process according to claim 7, wherein the coating emulsion further consists essentially of 10 to 70 g of said pH-sensitive polymer 30 to 90 g of a fatty acid containing 12 to 22 carbon atoms, and 0 to 20 g of an ether or ester of water-insoluble cellulose polymer.

* * * * *